United States Patent
Harnngton et al.

(10) Patent No.: US 7,246,312 B2
(45) Date of Patent: *Jul. 17, 2007

(54) SYSTEM AND METHOD FOR FITNESS EVALUATION FOR OPTIMIZATION IN DOCUMENT ASSEMBLY

(75) Inventors: Steven J Harnngton, Webster, NY (US); Lisa S. Purvis, Fairport, NY (US)

(73) Assignee: Xerox Corporation, Stamford, CT (US)

( * ) Notice: Subject to any disclaimer, the term of this patent is extended or adjusted under 35 U.S.C. 154(b) by 1122 days.

This patent is subject to a terminal disclaimer.

(21) Appl. No.: 10/209,626

(22) Filed: Jul. 30, 2002

(65) Prior Publication Data

US 2004/0024613 A1    Feb. 5, 2004

(51) Int. Cl.
*G06F 17/00* (2006.01)
(52) U.S. Cl. .................. 715/530; 715/517; 715/521
(58) Field of Classification Search ............. 715/517, 715/530, 521
See application file for complete search history.

(56) References Cited

U.S. PATENT DOCUMENTS

| | | | |
|---|---|---|---|
| 5,224,206 A | 6/1993 | Simoudis | |
| 5,517,621 A | 5/1996 | Fukui et al. | |
| 5,911,146 A * | 6/1999 | Johari et al. | 715/525 |
| 5,943,670 A | 8/1999 | Prager | |
| 6,014,678 A | 1/2000 | Inoue et al. | |
| 6,023,714 A | 2/2000 | Hill et al. | |
| 6,044,384 A | 3/2000 | Ishima et al. | |
| 6,134,563 A | 10/2000 | Clancey et al. | |
| 6,173,286 B1 | 1/2001 | Guttman et al. | 707/100 |
| 6,212,528 B1 | 4/2001 | Brophy et al. | |
| 6,668,354 B1 | 12/2003 | Chen et al. | |
| 2001/0051962 A1 | 12/2001 | Plotkin | |
| 2002/0040375 A1 * | 4/2002 | Simon et al. | 707/517 |
| 2002/0105537 A1 * | 8/2002 | Orbanes et al. | 345/733 |

(Continued)

OTHER PUBLICATIONS

Mariott, et al., "Fast and Efficient Client-Side Adaptivity for SVG", International World Wide Web Conference Proceedings of the eleventh international Conference on the World Wide Web, Honolulu, Hawaii, May 7-11, 2002, pp. 496-507.*

(Continued)

*Primary Examiner*—Doug Hutton
*Assistant Examiner*—Amelia Rutledge

(57) ABSTRACT

What is disclosed is a system and method for method for fitness evaluation to be used with a directly calculated or iterative optimization method for automatic document assembly. The method for fitness evaluation includes the steps of first capturing the creator's desire as a set of relative weights to be applied to an intent vector. Then, calculating for each candidate document assembly a set of value-property functions that evaluate properties considered to be factors in a good design (e.g., the balance of the document component on the page). Next, an inferred intent vector needs to be determined for each candidate document assembly as a function of the calculated value property function. Note that if the inferred intent vector is determined by a matrix multiplication applied to the vector of value property function results then the relative weights and intent definition matrix can be multiplied together to provide a weight vector that can be applied directly to the value properties. The desired weights are then applied to the inferred intents to derive a fitness measure by multiplying the intent vector components by weights and summing.

1 Claim, 2 Drawing Sheets

U.S. PATENT DOCUMENTS

| | | |
|---|---|---|
| 2004/0019847 A1 | 1/2004 | Purvis |
| 2004/0019850 A1 | 1/2004 | Purvis |
| 2004/0019851 A1 | 1/2004 | Purvis |
| 2004/0019852 A1 | 1/2004 | Purvis |
| 2004/0019855 A1 | 1/2004 | Purvis |
| 2004/0025109 A1 | 2/2004 | Harrington |
| 2004/0034613 A1 | 2/2004 | Purvis |
| 2004/0205472 A1 | 10/2004 | Purvis |
| 2004/0205588 A1 | 10/2004 | Purvis |
| 2004/0205609 A1 | 10/2004 | Milton et al. |

OTHER PUBLICATIONS

Ossenbruggen, et al., "Towards Second and Third Generation Web-Based Multimedia", International World Wide Web Conference Proceedings fo the tenth international conference on the World Wide Web, Hong Kong, 2001, pp. 479-488.*

Microsoft Computer Dictionary, 5$^{th}$ Ed., May 1, 2002, Microsoft Press, p. 548.*

Badros, et al., "A Constraint Extension to Scalable Vector Graphics", International World Wide Web Conference Proceedings of the tenth international conference on World Wide Web, pp. 489-498, Hong Kong, 2001.*

Mariott et al., "Fast and Efficient Client-Side Adaptivity for SVG", International World Wide Web Conference Proceedings of the Eleventh International Conference on World Wide Web, pp. 496-507, Honolulu, Hawaii.*

Dengler, E. Friedell, M., Marks, J., Constraint-Driven Diagram Layout, Proceedings of the 1993 IEEE Symposium on Visual Languages, pp. 330-335, Bergen, Norway, 1993 (diagrams).

Rousseau, F., Garcia-Macias, A., Valdeni de Lima, J., and Duda, A., *User Adaptable Multimedia Presentations for the WWW*, Electronic Proceedings from the 8$^{th}$ International World Wide Web Conference, 1999 (multimedia presentations).

Graf, W. H., *The Constraint-Based Layout Framework LayLab and Applications*, Electronic Proceedings of the ACM Workshop on Effective Abstractions in Multimedia, 1995 (flowcharts and yellow pages).

Kroener, A., *The Design Composer: Context-Based Automated Layout for the Internet*, Proceedings of the AAAI Fall Symposium Series: Using Layout for the Generation, Understanding, or Retrieval of Documents, 1999.

Badros G., Borning A., *The Cassowary Linear Arithmetic Constraint Solving Algorithm: Interface and Implementation*, University of Washington Technical Report, Jun. 4, 1998.

Purvis, Lisa, *Document Assembly and Transformation: A Survey*, XR&T/DITC/CADISYS/DI, Mar. 2001.

Holzner, Steven, Inside XML, New Riders Publishing, Indianapolis, IN, © 2001, pp. 68-73, 77-87, 402-412, 620-621, 626-643, 656-660 and 666-671.

Bradley, Keith, et al., "Case-Based User Profiling for Content Personalisation", Proc's of Int'l Conf on Hypermedia, Brusilovsky et al (eds), Adaptive Hyperm. & Adaptive Web-Based Systems Lecture Notes in CS, vol. 1892, Springer Verlag, © 2000 (11 pages).

Villard, Lionel, et al., "An Incremental XSLT Transformation Processor for XML Document Manipulation", WWW 2002, Honolulu, HI, May 7-11, 2002, pp. 474-485.

Mendes, Emilia, et al. "A Comparison of Case-Based Reasoning Approaches to Web Hypermedia Project Cost Estimation", WWW 2002, Honolulu, HI, May 7-11, 2002, pp. 272-280.

* cited by examiner

| AREA A WIDTH | AREA A HEIGHT | AREA A TOPLEFTX | AREA A TOPLEFTY | AREA B WIDTH | AREA B HEIGHT | AREA B TOPLEFTX | AREA B TOPLEFTY |

*FIG. 2*

SYSTEM AND METHOD FOR FITNESS EVALUATION FOR OPTIMIZATION IN DOCUMENT ASSEMBLY

RELATED APPLICATIONS

Attention is directed to commonly owned and assigned Application Numbers:

U.S. Ser. No. 10/202,046, filed Jul. 23, 2002 entitled "CONSTRAINT-OPTIMIZATION SYSTEM AND METHOD FOR DOCUMENT COMPONENT LAYOUT GENERATION".

U.S. Ser. No. 10/202,188, filed Jul. 23, 2002 entitled "CONSTRAINT-OPTIMIZATION SYSTEM AND METHOD FOR DOCUMENT COMPONENT LAYOUT GENERATION".

U.S. Ser. No. 10/202,183, filed Jul. 23, 2002 entitled "SYSTEM AND METHOD FOR CONSTRAINT-BASED DOCUMENT GENERATION".

U.S. Ser. No. 10/202,275, filed Jul. 23, 2002 entitled "SYSTEM AND METHOD FOR CONSTRAINT-BASED DOCUMENT GENERATION".

U.S. Ser. No. 10/202,207, filed Jul. 23, 2002 entitled "SYSTEM AND METHOD FOR DYNAMICALLY GENERATING A STYLE SHEET".

U.S. Ser. No. 10/202,247, filed Jul. 23, 2002 entitled "SYSTEM AND METHOD FOR DYNAMICALLY GENERATING A STYLE SHEET".

U.S. Ser. No. 10/202,227, filed Jul. 23, 2002 entitled "CASE-BASED SYSTEM AND METHOD FOR GENERATING A CUSTOM DOCUMENT".

U.S. Ser. No. 10/202,047, filed Jul. 23, 2002 entitled "CASE-BASED SYSTEM AND METHOD FOR GENERATING A CUSTOM DOCUMENT".

FIELD OF THE INVENTION

The present invention is directed to systems and methods to find document components and assemble them into a custom document such as a variable data document and, in particular, those systems and methods which use constraint-optimization approaches wherein the document, its content, components, and its requirements are expressed as a constraint optimization problem.

BACKGROUND OF THE INVENTION

Custom documents are documents that are personalized or tailored in some way to the particular user of the document. Two growing applications of custom documents are in the domain of variable data printing, as well as in web personalization.

Traditional approaches to custom document creation are non-automated and therefore user-intensive, and result in documents that are typically quite similar: the layout is the same for all instances, regardless of the available content pieces. Furthermore, the document creator is responsible for ensuring that the final document adheres to good design principles, and is therefore aesthetically pleasing. Thus the document creator himself typically creates the document template according to his preferred design criteria, which requires knowledge about document design and how to best achieve the desired qualities in a particular instance of the document.

Traditional creation of custom documents such as variable data documents requires expertise in many areas such as graphic arts and databases and is a time consuming process.

With the ever-increasing amount of information in the digital world and the amount of untrained users producing documents, old publishing tools often prove cumbersome and demanding whereas present dynamic digital environments demand tools that can reproduce both the contents and the layout automatically tailored to personal needs and which can enable novices to easily create such documents.

Known methods for automated creation of documents have focused more on particular types of documents, and not on modeling the problem in a general way in order to address all types of documents. Existing work provides methods for creating diagrams (see Dengler, E. Friedell, M., Marks, J., *Constraint-Driven Diagram Layout*, Proceedings of the 1993 IEEE Symposium on Visual Languages, pages 330-335, Bergen, Norway, 1993), or multimedia presentations (see Rousseau, F., Garcia-Macias, A., Valdeni de Lima, J., and Duda, A., *User Adaptable Multimedia Presentations for the WWW*, Electronic Proceedings from the 8$^{th}$ International World Wide Web Conference, 1999), or flowcharts and yellow pages (see Graf, W. H., *The Constraint-Based Layout Framework LayLab and Applications*, Electronic Proceedings of the ACM Workshop on Effective Abstractions in Multimedia, 1995). Others have explored automating the process of web document layout (see Kroener, A., *The Design Composer: Context-Based Automated Layout for the Internet*, Proceedings of the AAAI Fall Symposium Series: Using Layout for the Generation, Understanding, or Retrieval of Documents, 1999).

Known methods for a constraint-optimization approaches to document layout use a single optimization criterion: cost, and model their layout task as finding an ordering of stories and advertisements that can minimize the production cost as described in U.S. Pat. No. 6,173,286. The present invention differs in that it offers a more general model for representing a layout problem as a constraint optimization problem, enables the specification of multiple optimization criteria, and provides a process by which to combine required and optimization constraints in order to achieve a well-designed document.

What is needed in the arts in order to ensure that an automatically assembled document also meets desired aesthetic design criteria, is a way to model document creation as a multi-criteria optimization problem, allowing the specification of both required layout constraints as well as desired aesthetic qualities of the output document, and a means to automatically process this combination of hard and soft constraints to automatically generate a well-designed document.

SUMMARY OF THE INVENTION

What is disclosed is a system and method for method for fitness evaluation to be used with a directly calculated or iterative optimization method for automatic document assembly. The method for fitness evaluation includes the steps of first capturing the creator's desire as a set of relative weights to be applied to an intent vector. Then, calculating for each candidate document assembly a set of value-property functions that evaluate properties considered to be factors in a good design (e.g., the balance of the document component on the page). Next, an inferred intent vector needs to be determined for each candidate document assembly as a function of the calculated value property function. Note that if the inferred intent vector is determined by a matrix multiplication applied to the vector of value property function results then the relative weights and intent definition matrix can be multiplied together to provide a weight vector that can be applied directly to the value properties. The desired weights are then applied to the inferred intents to derive a fitness measure by multiplying the intent vector components by weights and summing. A genetic algorithm can be used as the iterative optimization method wherein each candidate document assembly is described as a genome and the fitness measure is then calculated for each genome and is used in determining its survival.

Other objects, advantages, and salient features of the invention will become apparent from the detailed description which, taken in conjunction with the drawings, disclose the preferred embodiments of the invention.

DESCRIPTION OF THE DRAWINGS

The preferred embodiment and other aspects of the invention will become apparent from the following detailed description when taken in conjunction with the accompanying drawings which are provided for the purpose of describing the invention and not for the limitation thereof, in which:

FIG. 2 illustrates the resulting genome after following through the example of FIG. 1.

DETAILED DESCRIPTION OF THE INVENTION

Figure 1:
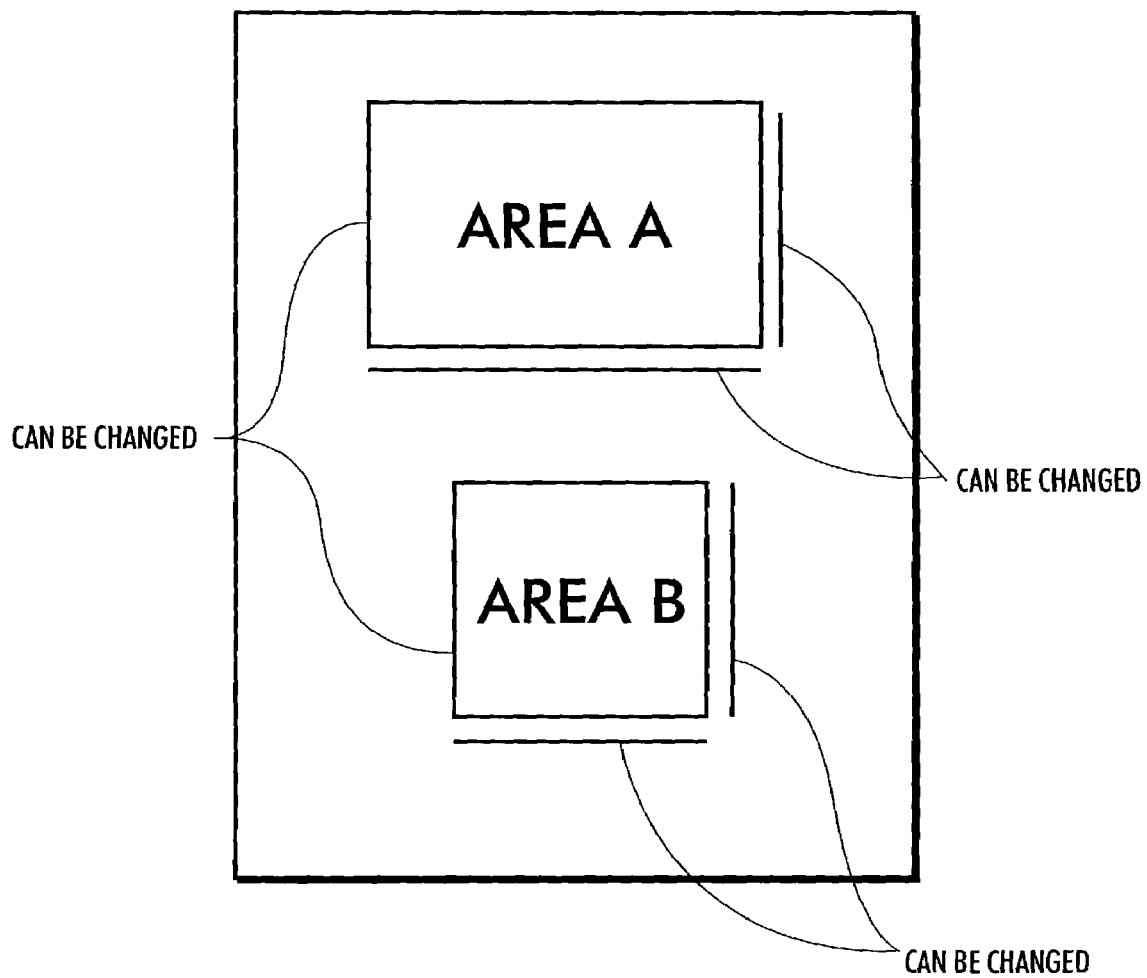
FIG. 1 illustrates a document template which specifies that there are two areas that should be filled with content: areaA and areaB, and which also specifies that the positions and sizes of areaA and areab can be changed.

What is disclosed is a system and method for specifying a custom document as a constraint optimization problem, and a method to automatically create the specified document using one of a set of many existing constraint optimization algorithms. The document is modeled as a constraint optimization problem which combines both required constraints with non-required design constraints that act as optimization criteria. One of a set of many existing constraint optimization algorithms is then used to solve the problem, resulting in an automatically generated document that is well designed because it has optimized some specified design criteria.

In particular, a document template is represented as a constraint optimization problem, and therefore contains a set of variables, a value domain for each variable, a set of required constraints, and a set of desired constraints (i.e. optimization functions).

In this invention, the areas of the document to be filled with content are modeled as problem variables, as are any parameters of the document that can be changed. As an example, consider the document template shown in FIG. 1. The template specifies that there are two areas that should be filled with content: areaA and areaB. The template also specifies that the positions and sizes of areaA and areaB can be changed. Thus, the problem variables for this example are: areaA, areaB, areaA-topLeftX, areaA-topLeftY, areaB-topLeftX, areaB-topLeftY, areaA-width, areaA-height, areaB-width, areaB-height.

The constraint optimization formulation further specifies that each problem variable has a value domain consisting of the possible values to assign to that variable. This invention teaches that for variables that are document areas to be filled with content (e.g., areaA and areaB of FIG. 1), the value domains are the content pieces that are applicable to each area. For variables that are document parameters, the value domains are discretized ranges for those parameters, so that each potential value for the parameter appears in the value domain e.g., 1..MAXINT. For variables whose value domains are content pieces, the default domain is set up to be all possible content pieces in the associated content database, which is specified in the document template.

The required constraints specify relationships between variables and/or values that must hold in order for the resulting document to be valid. The desired constraints specify relationships between variables and/or values that we would like to satisfy, but aren't required in order for the resulting document to be valid. Constraints may be unary (apply to one value/variable), binary (apply to two values/variables), or n-ary (apply to n values/variables), and in our invention are entered by the user as part of the document template. An example of a required unary constraint in the document domain is: areaA must contain an image of a castle. An example of a required binary constraint is: areaA-topLeftY+areaA-height<areaB-topLeftY. If we had another variable (areaC), an example of a required 3-ary constraint is: areaA-width+areaB-width >areaC-width. In a variable data application of this invention (one of many possible applications), the constraints would also refer to customer attributes (e.g., areaA must contain an image that is appropriate for customer1.age).

Desired constraints are represented as objective functions to maximize or minimize. For example, a desired binary constraint might be the objective function: f=areaA-width*areaA-height, to be maximized. If more than one objective function is defined for the problem, the problem becomes a multi-criteria optimization problem. If it is a multi-criteria optimization problem, we sum the individual objective function scores to produce the overall optimization score for a particular solution. We can furthermore weight each of the desired constraints with a priority, so that the overall optimization score then becomes a weighted sum of the individual objective function scores.

Any one of the known existing constraint optimization algorithms is then applied to create the final output document. This invention further describes a means to use a genetic algorithm (one of the many possible constraint optimization algorithms) for doing the constraint optimization and thereby automatically creating a final output document that adheres not only to the required constraints, but also to a set of desired constraints.

In our genetic algorithm formulation of constraint optimization for document creation, the genome is built such that each gene in the genome is a variable of the constraint problem. Following through our example from FIG. 1, the resulting genome is shown in FIG. 2. The unary constraints are used to set up the allowable value domains for each gene. These can be some default range, or input by the user.

In this invention, the fitness function is defined such that it returns a fitness of 0 for any population members that do not meet the required constraints, and for the members that do meet the required constraints, it returns a fitness score that is a sum of the scores of the individual desired constraints. For instance, if we have the required constraints:

C1: areaA-width<300

C2: areaB-width<300

And the desired constraints:

C3: areaA-width=areaB-width, to be maximized (ranges from 0 to 1)

C4: areaA-height=areaB-height, to be maximized (ranges from 0 to 1)

Examples of fitness function for these desired constraints are $$f3=1-|areaA\text{-width}-areaB\text{-width}|/(areaA\text{-width}+areaB\text{-width})$$

$$f4=1-|areaA\text{-height}-areaB\text{-height}|/(areaA\text{-width}+areaB\text{-height})$$

If we have a population member with areaA-width=350, areaA-height=350, areaB-width=400, areaB-height=200, the fitness function returns a score of 0. If, however, we have a population member with areaA-width=300, areaA-height=200, areaB-width=300, areaB-height=200, the fitness function returns a score of 2. If we have a population member with areaA-width=225, areaA-height=200, areaB-width=300, areaB-height=200, the fitness function returns a score of 1.875.

Our formulation also extends to allow weighting of the various desired constraints. Thus, the document creator can specify that certain desired constraints are more important than others. For instance, we could have constraint C3 weighted with an importance of 1.5, and C4 weighted with an importance of 0.5, meaning that the two objects having the same width is more important than the two objects having the same height. The fitness function's overall score is then computed as a weighted sum of the individual desired constraints.

For instance, if we have a population member with areaA-width=225, areaA-height=200, areaB-width=300, areaB-height=200, desired constraint C3 returns 0.875, which is multiplied by C3's weight of 1.5, to get 1.286. Desired constraint C4 returns 1, which is multiplied by C4's weight of 0.5, to get 0.5. The overall fitness score is then 1.125+0.5=1.786.

If, on the other hand, we have a population member with areaA-width=300, areaA-height=200, areaB-width=300, areaB-height=150, desired constraint C3 returns 1, which is multiplied by C3's weight of 1.5 to get 1.5. Desired constraint C4 returns 0.875, which is multiplied by C4's weight of 0.5, to get 0.438. The overall fitness score is then 1.5+0.438=1.938, thereby preferring the solution that violates C3 the least.

In the genetic algorithm implementation of this invention, we create an initial population of chromosomes by selecting values for each gene, and doing this for the desired number of population members. We evaluate each member of this population according to the fitness function, resulting in a score for each population member. We then select the most fit individuals (i.e., best fitness score) as parents for the new population, and create a new population from the parents using crossover/mutation operations. We iterate through populations until we reach a specified stopping condition (e.g., a certain number of iterations are complete, or until we have crossed a minimum threshold for the fitness function).

Thus, each genome is evaluated according to how well it satisfies or achieves the design qualities along with the other required constraints. This results in a generated document that not only satisfies the required constraints, but that is also optimized for the specified design qualities.

Further regarding fitness evaluation, during the creation of a document the document creator makes many decisions (e.g., what size font to use, what type of font, how long the lines should be, etc.) where presumably these decisions are made in order to achieve certain value properties in the document (e.g., low cost, balanced, readable, etc.). There are many such properties to consider when creating a document, and thus the need for many decisions by the author. The intent lies in the relative importance of the various value properties. Depending on intent, certain properties will be strengthened while others will be sacrificed. Intent information to optimize document creation and formatting was explored. The idea that intents could be used to define a linear combination of measured value properties. This can be expressed as: I=A V where I is a vector of intent coordinates inferred from the properties of the document, V is a vector of value properties and A is a matrix relating the value properties to intents. This suggests that document properties could be adjusted to produce value properties that in turn generate a desired intent. Thus, $f_1=|I-I_d|$ is a fitness function that tells how well the document matches the desired intent $I_d$. Minimizing this function can be used to generate the document or its presentation. However, this does not form a document solution with value properties leading to intent values greater than the original desired intent $I_d$. In some cases, it may be the relative strengths of the intents that is important rather than their absolute measure. Thus an alternative fitness function utilizing the weighted sum of the inferred intents is preferred and can be defined as: $f_2=w$ I=w A V where w is the desired proportion or weighting of the intents. Maximizing this function allows the various intents to be maximized but when increasing one intent results in a decrease of another intent then the weighting factors control the final proportions chosen. This fitness function will optimize value properties and use the intent weights to select which property to optimize when increasing one decreases another. In addition, a genetic algorithm can be used where the fitness function is a weighted sum of the desired properties of the document. Further, since genomes define document layouts and the genetic algorithm determines which genomes survive by evaluating their fitness then, by using the fitness function of the genetic algorithm, the generated solutions become closer and closer to the creator's intent.

The method for fitness evaluation includes the steps of first capturing the creator's desire as a set of relative weights to be applied to an intent vector. Then, calculating for each candidate document assembly a set of value-property functions that evaluate properties considered to be factors in a good design (e.g., the balance of the document component on the page). Next, an inferred intent vector needs to be determined for each candidate document assembly as a function of the calculated value property function. Note that if the inferred intent vector is determined by a matrix multiplication applied to the vector of value property function results then the relative weights and intent definition matrix can be multiplied together to provide a weight vector that can be applied directly to the value properties. The desired weights are then applied to the inferred intents to derive a fitness measure by multiplying the intent vector components by weights and summing. A genetic algorithm can be used as an iterative optimization method wherein each candidate document assembly is described as a genome and the fitness measure is then calculated for each genome and is used in determining its survival.

The system and method of the present invention has many advantages over the prior art. Whereas the current constraint satisfaction approaches often require many low-level layout constraints to be specified in order to achieve a reasonable result, the genetic algorithm approach disclosed herein allows a specification of a few high-level desired constraints and qualities—a much more intuitive and less user-demanding process. Another advantage of the constraint optimization approach described herein is that it can find pleasing solutions for any combination of content thereby enabling more dynamic custom document instances. In addition, selection of content can be influenced by the design criteria that is included in the solving process by creating genes that specify the number of items to include for each content area and, as the gene value varies, the content items included vary as well. Another advantage of the present constraint-optimization system and method is that the various aesthetic criteria can be weighted and result in a different output document based on the weightings (e.g., a different output document would be generated if compactness was heavily weighted than if page utilization was heavily weighted).

While the invention is described with reference to a particular embodiment, this particular embodiment is intended to be illustrative, not limiting. Various modifications may be made without departing from the spirit and scope of the invention as defined in the amended claims. Modifications and alterations will occur to others upon reading and understanding this specification; therefore, it is intended that all such modifications and alterations are included insofar as they come within the scope of the appended claims or equivalents thereof.

What is claimed is:

1. A system for evaluating, by generating a fitness measure value, a set of variable data documents generated by an automatic document assembly process, a set of variable data documents being a set of documents having a portion corresponding to a predetermined content and a portion corresponding to a variable content, the predetermined content being the same in each document of the set of variable data documents, comprising:
    an input device to input document specifications for a set of variable data documents to be generated, the document specifications being represented as a set of relative weights;
    a processor to generate a set of variable data documents;
    said processor executing, for each variable data document, a set of value-property functions to generate a set of value properties, said set of value-property functions evaluating properties representing a good design;
    said processor determining an inferred intent vector for each variable data document as a function of the set of calculated set of value properties, said inferred intent vector is determined by a matrix multiplication applied to a vector of value properties; and
    said processor generating a fitness measure value by multiplying components of the inferred intent vector by a corresponding relative weight from the set of relative weights to generate a set of products and summing the set of products.

* * * * *

UNITED STATES PATENT AND TRADEMARK OFFICE
CERTIFICATE OF CORRECTION

PATENT NO. : 7,246,312 B2  Page 1 of 1
APPLICATION NO. : 10/209626
DATED : July 17, 2007
INVENTOR(S) : Steven J. Harrington and Lisa S. Purvis It is certified that error appears in the above-identified patent and that said Letters Patent is hereby corrected as shown below:

In the cover page, item (12) Harrngton et al. should read Harrington et al.
item (75) Steven J. Harrngton should read Steven J. Harrington Signed and Sealed this Twenty-first Day of August, 2007

JON W. DUDAS
*Director of the United States Patent and Trademark Office*